(12) United States Patent
Liehs

(10) Patent No.: US 6,425,397 B1
(45) Date of Patent: Jul. 30, 2002

(54) APPLICATOR RING FOR CONDOMS

(76) Inventor: Reinhard Liehs, Hans-Sachs-Gasse 14, A-5020, Salzburg (AT)

( * ) Notice: Subject to any disclaimer, the term of this patent is extended or adjusted under 35 U.S.C. 154(b) by 0 days.

(21) Appl. No.: 09/582,066

(22) PCT Filed: Dec. 22, 1998

(86) PCT No.: PCT/AT98/00318
§ 371 (c)(1),
(2), (4) Date: Jul. 20, 2000

(87) PCT Pub. No.: WO99/32058
PCT Pub. Date: Jul. 1, 1999

(30) Foreign Application Priority Data

Dec. 22, 1997 (AT) ................................................ 2168/97

(51) Int. Cl.[7] .................................................. A61F 6/02
(52) U.S. Cl. ........................... 128/842; 128/844; 206/69
(58) Field of Search ................................. 128/842, 844, 128/918; 604/347–353; 206/69

(56) References Cited

FOREIGN PATENT DOCUMENTS

| DE | 823318 | 10/1951 |
|----|--------|---------|
| DE | 4241441 | 6/1994 |
| FR | 2727858 | 6/1996 |
| WO | 9321873 | 11/1993 |
| WO | 9801095 | 1/1998 |

*Primary Examiner*—Michael A. Brown
(74) *Attorney, Agent, or Firm*—Dykema Gossett PLLC

(57) ABSTRACT

An applicator ring for condoms with a ring that keeps the condom tense includes at least three connecting rods articulated on the ring, a retaining claw being pivotally fixed at the end of each rod and designed to clutch the roll of the condom.

13 Claims, 6 Drawing Sheets

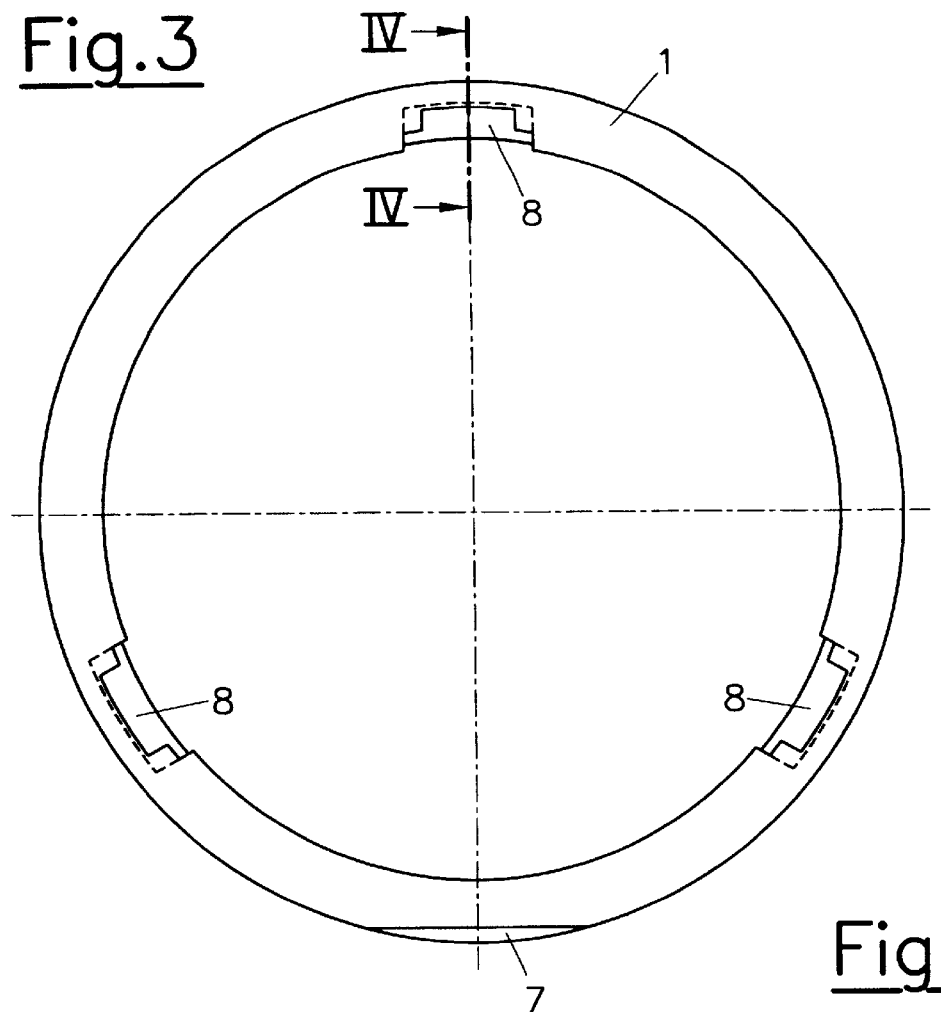
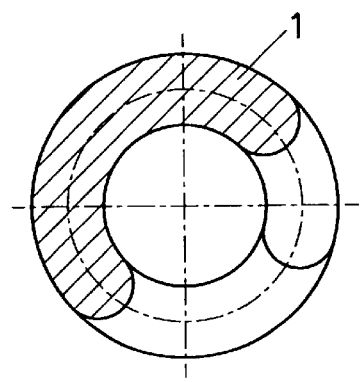
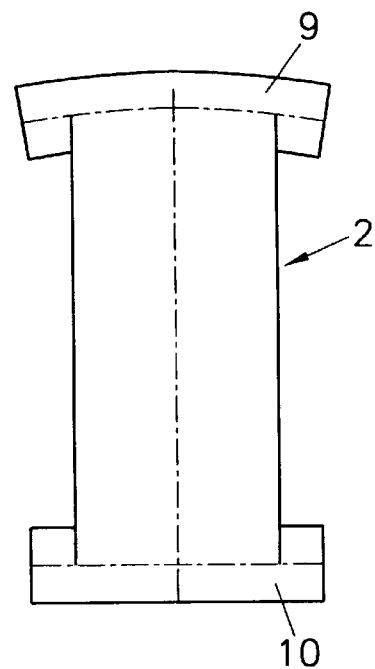

APPLICATOR RING FOR CONDOMS

BACKGROUND OF THE INVENTION

1. Field of the Invention

The present invention relates to an applicator ring for condoms with a ring that keeps the condom tense.

2. The Prior Art

Up to now, condoms are put on the market in a rolled state, packaged in envelopes or foils. For use, the condoms are applied by hand once the packaging has been opened. The possibilities to use them incorrectly are multiple, which jeopardizes the safety of contraception. First of all, the condoms may be mechanically damaged by finger nails or the like during the process of opening the packaging by tearing. Furthermore, when the condom is rolled up, it is not directly evident in which direction it has to be unrolled. By trying to unroll it in the wrong direction, the risk of damage is again given. Additionally, the protective effect is reduced since a potential spermicide is only coating one side of the condom. The risk is thereby given that semen gets on the outer side of the condom, which obviously destroys the intended effect. The unrolling the condom moreover constitutes a disagreeable or unwanted procedure for many users.

The WO 93/21873 discloses a tool for applying condoms that consists of an annular frame with a tub-shaped cross section onto which a rolled-up condom may be placed. When the ring, with the condom applied, is pulled over the penis, the condom unrolls in the process. on one side, the disadvantage of this embodiment is that the ring has to have a relatively great diameter to fit over the penis, since it constitutes an essentially rigid component part. The mounted condom is hereby stretched to a great extent and this extension involves the risk of damage. On the other side, guidance of the condom by this device is relatively bad and the condom may slide out untimely.

Furthermore, an applicator for contraceptive devices is known from DE 42 41 441 A, by means of which the contraceptive device is essentially unrolled by means of negative pressure. In practice, such devices proved not to be reliably operative. Additionally, the creation of the negative pressure on one side of the condom by means of movable cylinders or by any other means (a pump for example) and the application on the penis on the other side of the condom cannot be coordinated in a precise manner.

According to a previous suggestion of the applicant, a condom is attached to a ring by means of elastic or articulated holding and unrolling devices, rolls being arranged thereon so as to face each other in pairs. The manufacturing of the rolls is relatively complicated so that there is a need for a device that is reasonably priced and simple in construction.

SUMMARY OF THE INVENTION

It is the object of the present invention to provide an applicator ring for condoms that avoids the above-mentioned drawbacks and that permits to apply condoms in a safe, reliable and convenient way. It is another object of the invention to provide a device that further simplifies the procedure of application of condoms with the help of such an applicator ring.

According to the invention, the solution of this object is to articulate at least three connecting rods on the ring, a retaining claw being pivotally attached at the end of each rod and being designed to clutch the roll of the condom. Thanks to the design according to the invention, the condom is held in the ring in a flexible and yielding way so that the application of the condom no longer constitutes an irksome procedure for the user.

The essential feature of the present invention is that the condom is held by three claws that are evenly spaced on the circumference of the ring. If necessary, more than three claws, five for example, may be provided. The aperture of the condom is thus securely kept in a position that is suitable for introducing the penis therein. The overall structure of the applicator ring is so flexible that the adaptation to the most varied conditions of use occurs automatically and smoothly.

The retaining claws are preferably provided with a cylindrical through hole, the diameter of which being greater than the diameter of the roll of the condom when it is rolled up and the through hole is preferably provided in longitudinal direction with a slot serving to unroll the condom, said slot being smaller in width than the thickness of the roll of the rolled-up condom. The rolled-up condom may thus be securely held in the through hole and can only be released through the slot when the roll has become smaller by unrolling. The retaining force gets smaller as the condom is unrolled. If the applicator ring is to be pulled off an only partially unrolled condom, this may be done by a small jerk. Its removal is made even more easy by the pivotal fixation of the retaining claw.

In a first preferred embodiment of the invention, the claws each consist of a component part with a hook-shaped cross section and of a covering part that may be fastened to the hook-shaped part. The covering part is preferably fastened onto the hook-shaped part by means of a snap. In this embodiment, the condom may easily be inserted during manufacturing as long as the covering part has not yet been mounted. By latching the covering part or by fastening it by another means, the condom gets locked in the through hole.

As an alternative, the retaining claws may be made in one piece out of a flexible material. In this embodiment, the number of piece parts of the applicator ring is reduced, which further simplifies the process of manufacturing. During the assembling process, the condom may be pressed into the through hole by an appropriate automatic packaging machine, whereby the claw is being deformed. The retaining claws may for example be provided with apertures so that the claws may be opened for inserting the packaged condom by the introduction of pins. An automatic packaging machine may thus be used in a particularly advantageous manner. In such an embodiment, the overall applicator ring in particular may be made in one piece out of plastic, wherein the corresponding articulations are formed by places of reduced thickness of material.

It is of particular advantage to have the connecting rods pivotally arranged on the applicator ring between a first and a second end position, wherein, in the first end position, they are essentially level with the plane of the applicator ring, whereas in the second end position they lie essentially at right angles to the plane of the applicator ring and to have the slot of the retaining claws oriented in the direction of the pivoting movement of the corresponding connecting rod. The unrolling procedure may thus be accomplished with hardly any friction in a particularly easy manner.

In order to meet all the legal requirements and to increase safety, it is suitable to package the rings—in exactly the same way as the individually packaged condoms. In order to make the unpacking procedure more convenient, the ring may be provided on its outer circumference with a cutting edge that cuts open the packaging when pressure is exerted.

The present invention also relates to a device for unpacking applicator rings as they have been described herein above with a housing, in which a tab is slidably guided. Corresponding embodiments are indicated in the description of the drawing.

A "condom pistol" as described in WO 98/01095 may be used as an alternative.

BRIEF DESCRIPTION OF THE DRAWINGS

The invention will be explained more explicitly in the following with the help of the embodiments illustrated in the figures.

FIG. 3 is a view of the ring,

FIG. 4 is a sectional view along the line IV—IV in FIG. 3,

FIG. 5 is an enlarged view of a connecting rod,

DETAILED DESCRIPTION OF THE PREFERRED EMBODIMENTS

Figure 1:
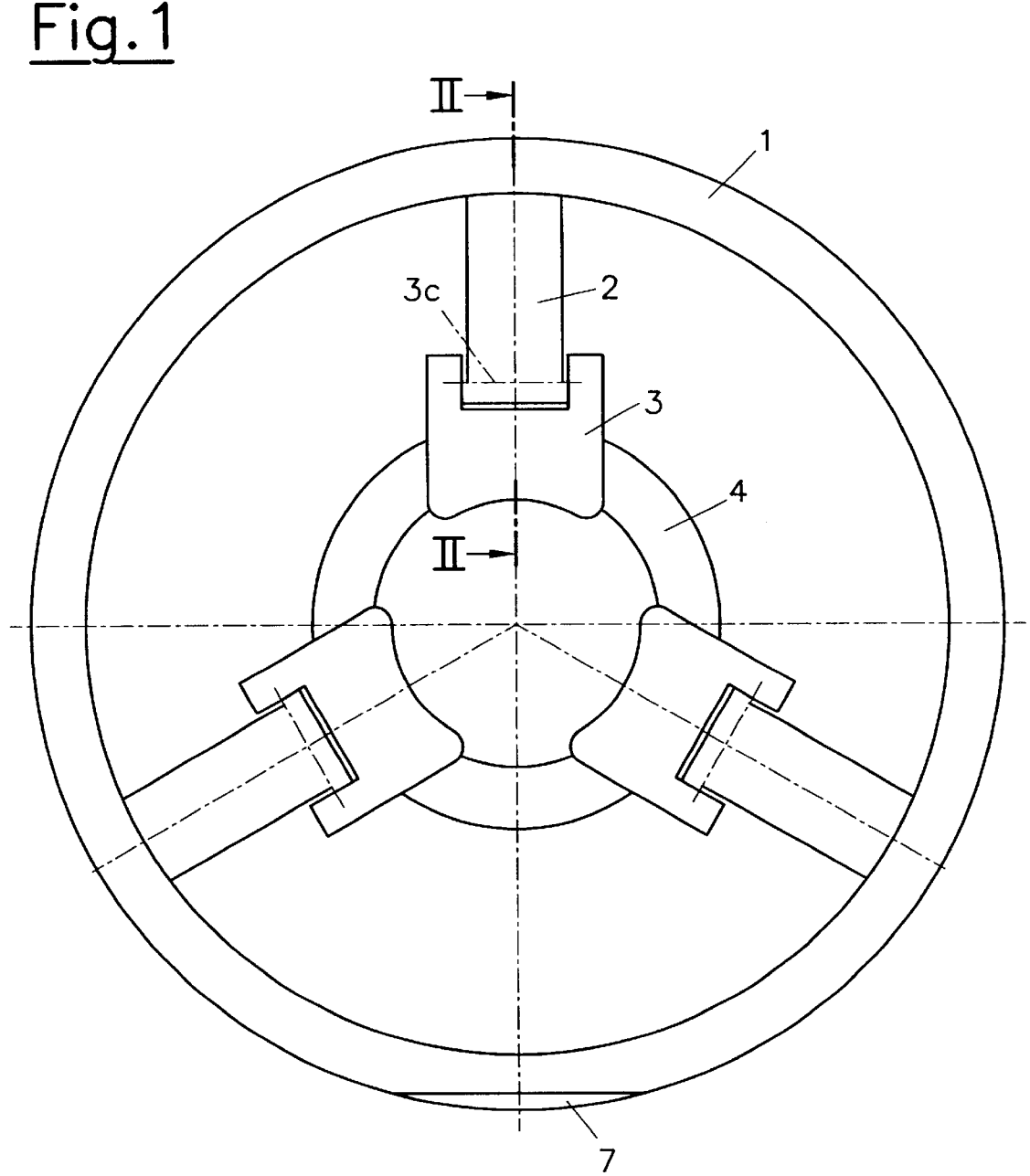
FIG. 1 shows a top view of an applicator ring according to the invention.
Figure 2:
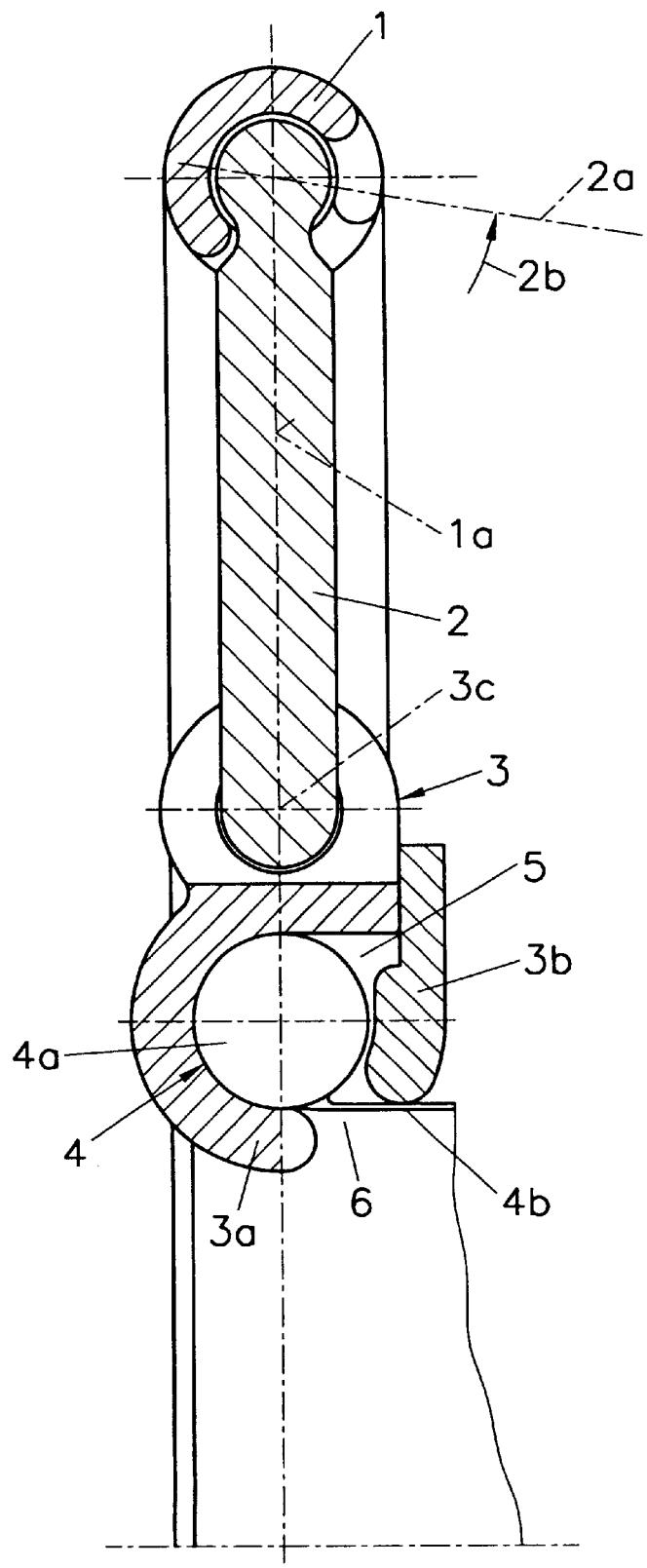
FIG. 2 is an enlarged sectional view along the line II—II.

The applicator ring of FIG. 1 consists of a ring 1 onto which three connecting rods 2 are hinged in regular angular intervals. A retaining claw 3 that holds the condom 4 is provided at the inner end of each connecting rod 2. The retaining claw 3 is arranged on the corresponding connecting rod 2 so as to be rotatable about an axis 3c. FIG. 2 shows that the retaining claws 3 consist of a hook-shaped piece part 3a and of a covering part 3b, which is attached to the piece part by means of a snap. The hook-shaped part 3a and the covering part 3b include a through hole 5, wherein a slot 6 is formed between the hook-shaped part 3a and the covering part 3b. The roll 4a of the condom 4 is located in the through hole 5 and the pouch-like section 4b of the condom 4 is guided outward via the slot 6. FIG. 2 also shows that the connecting rod 2 is arranged between the first end position as it is shown in this Figure and an end position, which is sketched by the central line 2a in such a manner that it may pivot in the direction of the arrow 2b. It is obvious that in the second end position the connecting rods 2 are standing nearly upright on the plane 1a of the applicator ring 1. At one location on its outer periphery, the ring 1 has a cutting edge 7 that cuts open the packaging when it is pulled in this direction. The cutting edge 7 may be formed at one location on the outer periphery like in the variant illustrated in the Figure herein, it may be formed over the whole circumference, too though.

FIG. 3 shows that bearings 8 are provided on the ring 1 at three evenly spaced locations on the circumference in order to keep the connecting rods 2 articulated. The configuration of the bearings 8 is represented in a sectional view in FIG. 4. The connecting rods 2 have a curved peg 9 and a straight peg 10. The curved peg 9 is designed so as to engage the bearings 8 of ring 1. The straight peg 10 holds the corresponding retaining claw 3.

Figure 6:
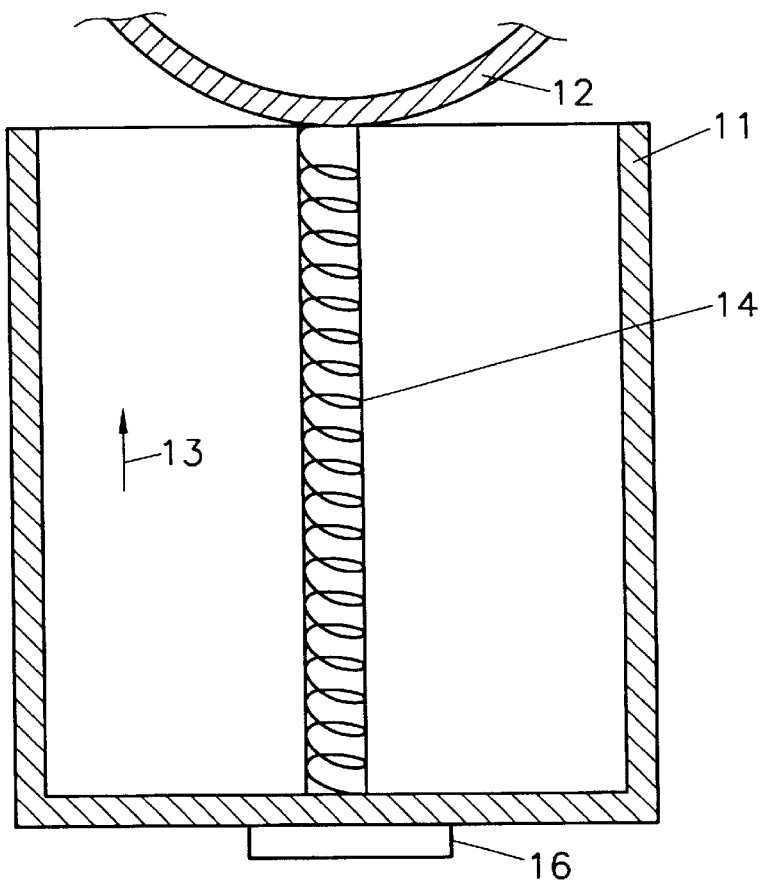
FIGS. 6 and 7 show a device for unpacking an applicator ring.
Figure 7:
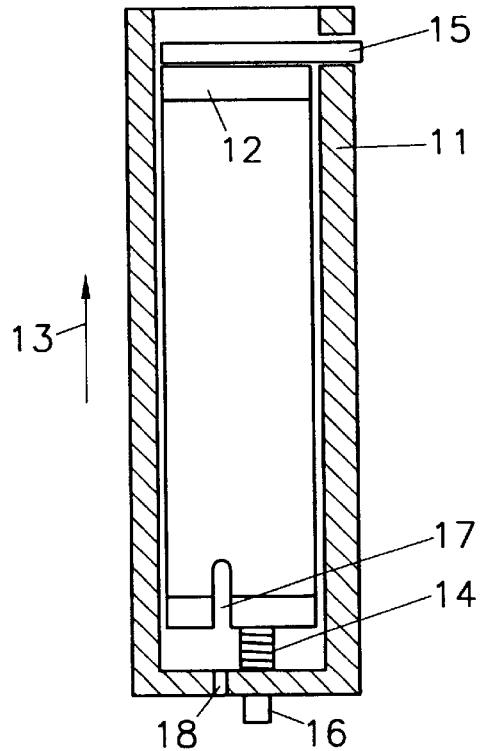

The FIGS. 6 and 7 show a variant of the device for unpacking applicator rings. The device according to the invention consists of a housing 11 holding a tab 12, which is supported in such a way that it may slide in the direction of the arrow 13. In FIG. 6, the tab 12 is shown in its drawn out position, whereas in FIG. 7 the tab 12 is completely inside the housing 11. A spring 14 pretensions the tab 12 in upward direction. In the position illustrated in FIG. 7 the tab 12 is kept in the position shown by means of a locking pin 15.

To allow removal of the packaging of the applicator ring that is not illustrated herein, a first opening 17 is provided in the lower area of the tab 12, a second opening 18 being provided in the housing 11 in alignment with this first opening 17. The openings 17, 18 may be conical toward the top so that a suitable bracket of the packaging of the applicator ring may be guided downward out through these openings 17, 18. The bracket may be bent and fixed on the knob 16. upon removal of the locking pin 15, the spring 14 pushes the tab 12 together with the attached applicator ring upward, the packaging however being retained at the bottom. The cutting edge 7 arranged in the upper area of the applicator ring cuts the packaging open from the inside so that the tab 12 with the now unpacked applicator ring may now reach the position illustrated in FIG. 6. The packaging hereby remains inside the housing 11. Subsequently, it may be completely pulled out through the slots 17, 18 and be disposed of.

Figure 8:
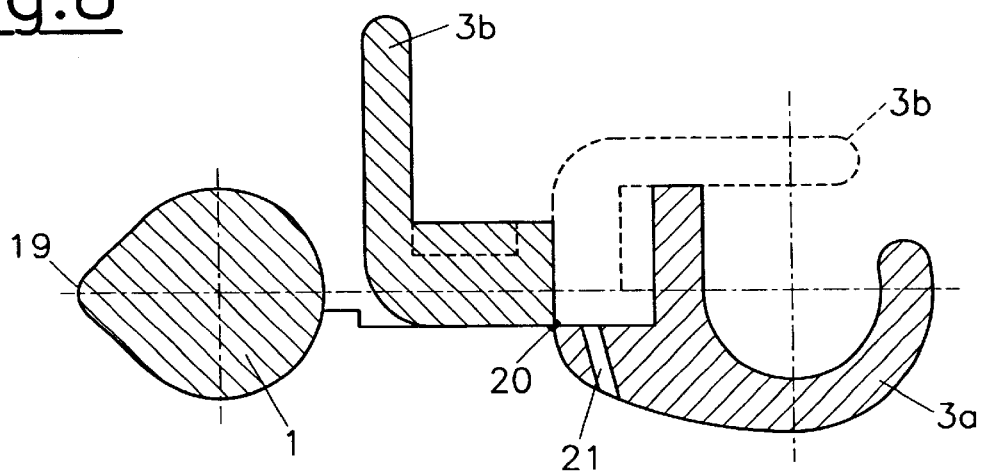
FIGS. 8 and 9 are a sectional view and a top view respectively of another embodiment of an applicator ring.
Figure 9:
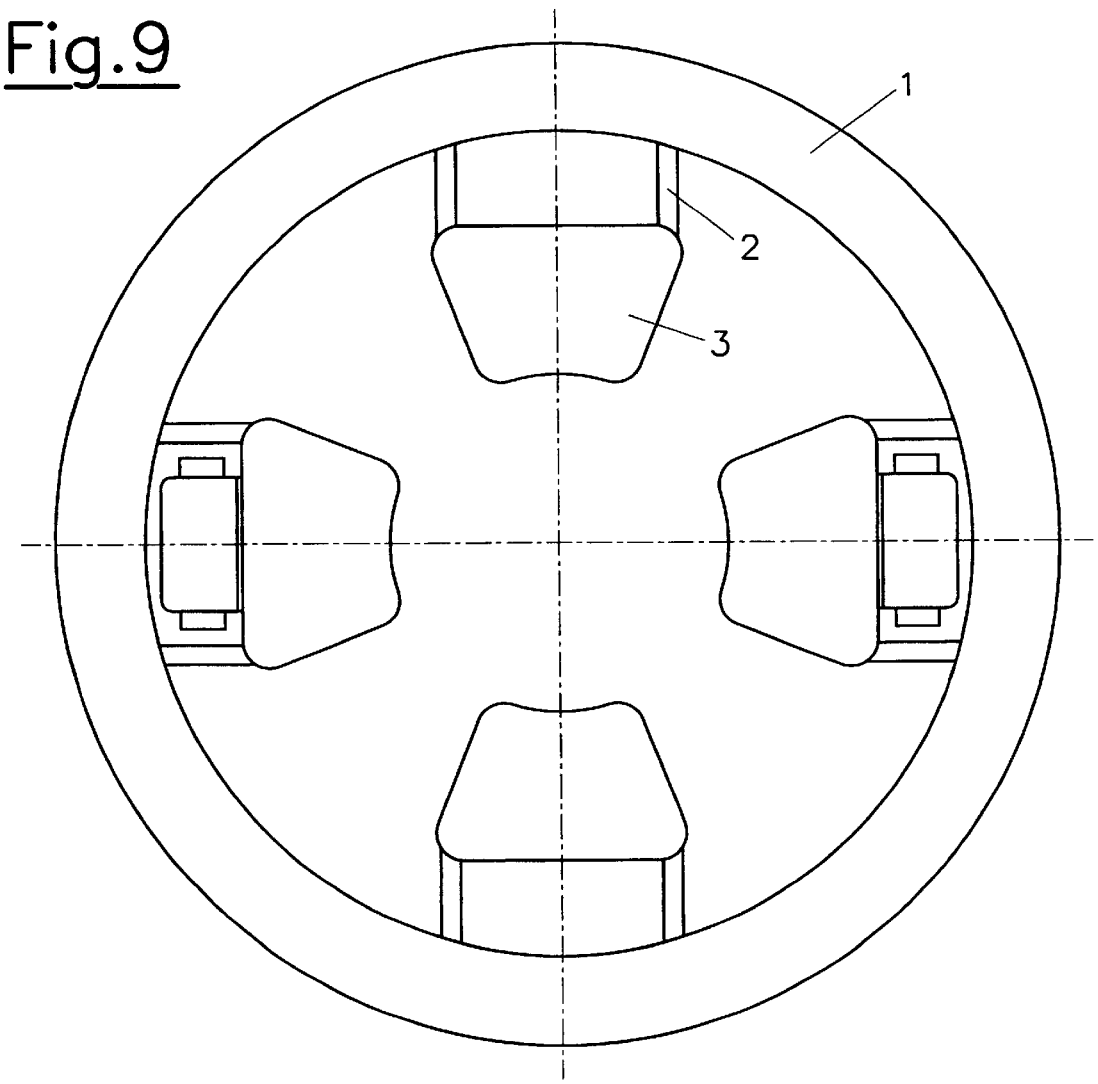

The variant illustrated in the FIGS. 8 and 9 has two elastic connecting rods 2 attached on the ring 1 for each retaining claw 3. As opposed to the variant described herein above, the ring 1 has, on its outer circumference, a cutting edge 19 serving to open by an appropriate pressure the not shown packaging of the applicator ring.

The retaining claw 3 consists of a hook-shaped part 3a and of a covering part 3b that is shown pulled out in the position allowing the condom to be inserted, whereas the position upon insertion of the condom is shown in dashed lines. The covering part 3b is articulated on a thinner part of material 20 on the hook-shaped part 3a and is kept in the closed position (dashed lines) by the elastic forces of the material. A bore 21 is provided in the lower area of the hook-shaped piece part 3a, so that a not shown pin may be introduced during the procedure of insertion, said pin serving to press the covering part 3b there upon. Then, the condom may conveniently be inserted from the top.

Figure 10:
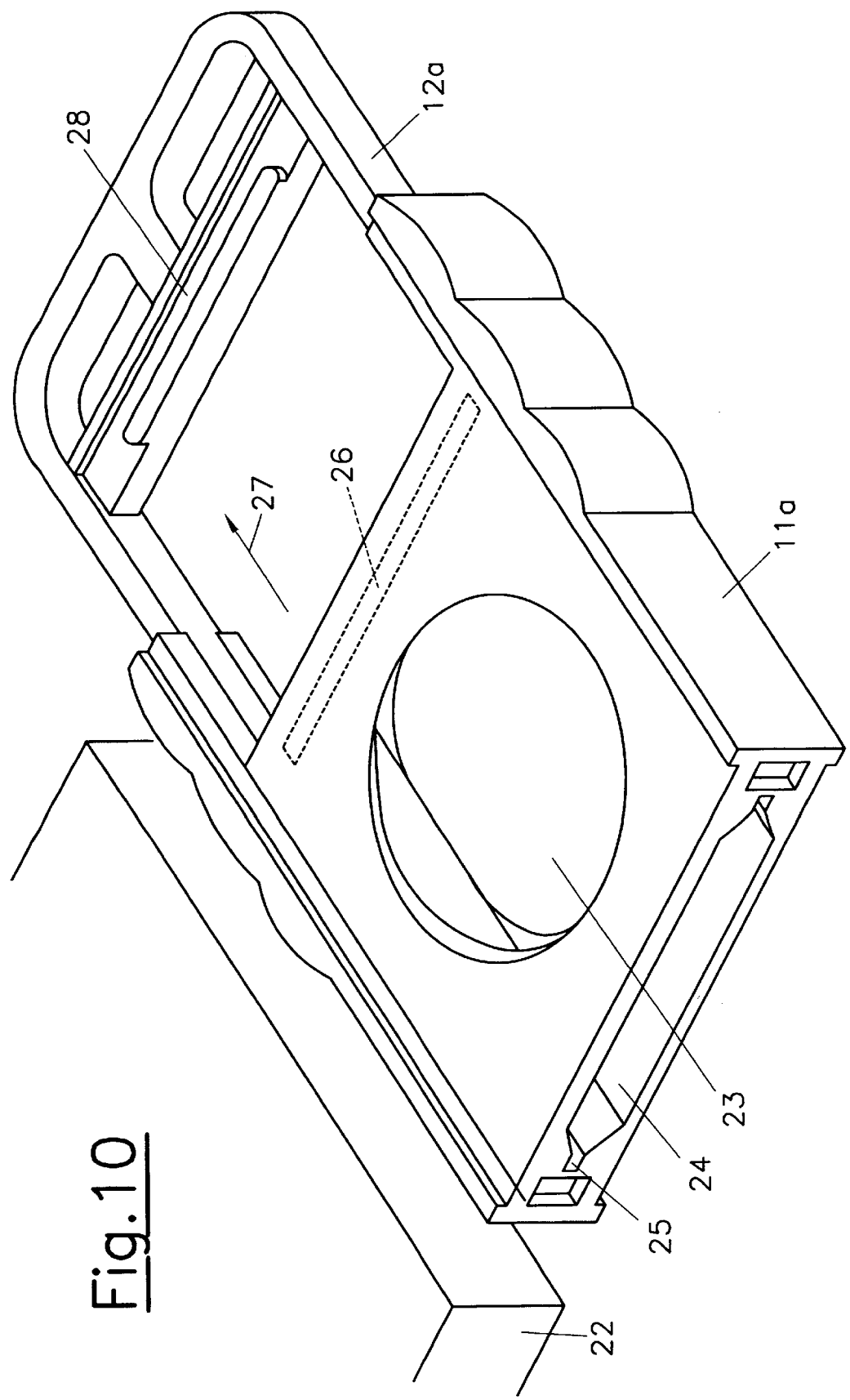
FIG. 10 shows a variant of a device for unpacking an applicator ring.

In the device of FIG. 10, a tab 12a is slidably arranged in a housing 11a. A cover, which is shown only in parts, serves to close the device prior to use. An approximately circular recess 23 is provided in the housing 11a, through which the penis may be introduced in the process of positioning the condom. The applicator ring described above is kept in a space 24 that is provided on its sides with grooves 25 for the projecting ends of the packaging. The space 24 is closed in the opening direction of the tab (arrow 27) except for a slot 26 through which a bracket of the packaging of the applicator ring may come through. The bracket that has come through is kept in place on a retaining surface 28 of the tab 12a and is pulled off by pulling out the tab 12a in the direction of the arrow 27. The cutting edge 19 of the applicator ring thereby cuts the packaging open on the opposite side. Upon removal of the packaging, the device is ready for use.

The present invention permits to put on the market condoms that are packaged in such a manner that it is hardly possible to use them incorrectly. The safety of contraception is thus considerably improved.

What is claimed is:

1. Applicator ring for condoms with a ring that keeps the condom tense, wherein at least three connecting rods are articulated on the ring, an elastic retaining claw consisting of two locking parts formed integral to the corresponding connecting rod pivotally attached at the end of each rod and designed to clutch the roll of the condom, the retaining claws being provided with means for pressing one of the two locking parts against the other of the two locking parts and means serving to achieve a position to insert the condom and being pretensioned in the position encompassing the condom.

2. Applicator ring according to claim 1, wherein the retaining claws are provided with a cylindrical through hole, the diameter of which is greater than the diameter of the roll of the condom when it is rolled up, and wherein the through hole is provided in longitudinal direction with a slot serving to unroll the condom, said slot being smaller in width than the thickness of the roll of the rolled-up condom.

3. Applicator ring according to claim 1, wherein the retaining claws each consist of a component part of a hook-shaped cross section and a covering part that may be fastened to the hook-shaped part.

4. Applicator ring according to claim 3, wherein the covering part is fastened on the hook-shaped part with a snap.

5. Applicator ring according to claim 1, wherein a cutting edge designed to open a packaging is formed on the outer periphery of the ring.

6. Applicator ring according to claim 1, wherein the connecting rods are pivotally arranged on the applicator ring between a first and a second end position, wherein, in the first end position, they are level with a plane of the applicator ring, whereas in the second end position they are essentially at right angles to the plane of the applicator ring, and the retaining claws each define a slot oriented in the direction of pivotal movement of the corresponding connecting rod.

7. Device for unpacking applicator rings according to claim 1 with a housing in which a tab is slidably guided, wherein the housing is designed to receive the packaged applicator ring and the tab is provided with a retaining surface for pulling off the packaging.

8. Device according to claim 7, wherein at least one of the tab and the housing is provided with a slot serving to pull off the packaging.

9. Device according to claim 7, wherein the housing holds a space designed to receive packaging containing the applicator ring and is provided with grooves for proud ends of the packaging.

10. Device for unpacking applicator rings according to claim 1 with a housing in which a tab is slidably guided, wherein the tab is designed to receive the packaged applicator ring and the housing is provided with a retaining surface for pulling off the packaging.

11. Device according to claim 10, including an expelling member for moving the tab, the moving direction of the expelling member being essentially arranged at right angles to an axis of the applicator ring.

12. Device according to claim 11, wherein the drive of the expelling member is mechanical.

13. Applicator ring for condoms with a ring that keeps the condom tense, wherein at least three connecting rods are articulated on the ring, an elastic retaining claw consisting of two locking parts formed integral to the corresponding connecting rod pivotally attached at the end of each rod and designed to clutch a roll of the condom, the retaining claws being provided with a bore for receiving a pin for pressing one of the two locking parts against the other of the two locking parts and means serving to achieve a position to insert the condom and being pretensioned in the position encompassing the condom.

* * * * *